US008032399B2

(12) United States Patent
Brown

(10) Patent No.: US 8,032,399 B2
(45) Date of Patent: *Oct. 4, 2011

(54) TREATMENT REGIMEN COMPLIANCE AND EFFICACY WITH FEEDBACK

(75) Inventor: Stephen J. Brown, Woodside, CA (US)

(73) Assignee: Health Hero Network, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/714,720

(22) Filed: Mar. 1, 2010

(65) Prior Publication Data

US 2010/0161350 A1   Jun. 24, 2010

Related U.S. Application Data

(63) Continuation of application No. 10/233,296, filed on Aug. 30, 2002, now Pat. No. 7,970,620, which is a continuation-in-part of application No. 09/304,477, filed on May 3, 1999, now Pat. No. 6,189,910, application No. 12/714,720, which is a continuation of application No. 11/845,317, filed on Aug. 27, 2007, now Pat. No. 8,015,033, which is a continuation-in-part of application No. 09/237,194, filed on Jan. 26, 1999, which is a continuation of application No. 08/481,925, filed on Jun. 7, 1995, now Pat. No. 5,899,855, which is a continuation of application No. 08/233,397, filed on Apr. 26, 1994, now abandoned.

(51) Int. Cl.
 *G06Q 50/00* (2006.01)
 *G06Q 10/00* (2006.01)

(52) U.S. Cl. .............................. 705/3; 705/2

(58) Field of Classification Search ............... 705/2–3
 See application file for complete search history.

(56) References Cited

U.S. PATENT DOCUMENTS

| 3,808,502 | A | 4/1974 | Babilius |
| 3,910,257 | A | 10/1975 | Fletcher et al. |
| 4,051,522 | A | 9/1977 | Healy et al. |
| 4,110,918 | A | 9/1978 | James et al. |
| 4,130,881 | A | 12/1978 | Haessler et al. |
| 4,151,407 | A | 4/1979 | McBride et al. |

(Continued)

FOREIGN PATENT DOCUMENTS

EP   0251520   1/1988

(Continued)

OTHER PUBLICATIONS

1999_07_00_Wilkins, Aaron. Expanding Internet access for health care consumers, Health Care Management Review, Summer, Jul. 1999, 24-30.

(Continued)

*Primary Examiner* — Gerald J. O'Connor
*Assistant Examiner* — Sheetal R Rangrej
(74) *Attorney, Agent, or Firm* — Christopher P. Maiorana, PC

(57) ABSTRACT

A method and system for interaction with a community of individuals, relating to compliance with and effectiveness of treatment regimens, including supply and use of pharmaceuticals, using a protocol or other intelligent message which acts in place of a service provider and which is capable of collecting or imparting information to patients in place thereof. Individuals interact with the protocol or intelligent message to provide assistance in all aspects of treatment regimen compliance, data collection, supply or delivery, review and modification.

20 Claims, 3 Drawing Sheets

U.S. PATENT DOCUMENTS

| | | | |
|---|---|---|---|
| 4,173,971 A | 11/1979 | Karz | |
| 4,253,521 A | 3/1981 | Savage | |
| 4,296,756 A | 10/1981 | Dunning et al. | |
| 4,347,568 A | 8/1982 | Giguere et al. | |
| 4,347,851 A | 9/1982 | Jundanian | |
| 4,360,345 A | 11/1982 | Hon | |
| 4,428,733 A | 1/1984 | Kumar-Misir | |
| 4,546,436 A | 10/1985 | Schneider et al. | |
| 4,576,578 A | 3/1986 | Parker et al. | |
| 4,625,733 A | 12/1986 | Saynajakangas | |
| 4,674,652 A * | 6/1987 | Aten et al. | 221/3 |
| 4,706,207 A | 11/1987 | Hennessy et al. | |
| 4,712,562 A | 12/1987 | Ohayon et al. | |
| 4,729,381 A | 3/1988 | Harada et al. | |
| 4,730,253 A | 3/1988 | Gordon | |
| 4,731,726 A * | 3/1988 | Allen, III | 600/300 |
| 4,749,354 A | 6/1988 | Kerman | |
| 4,751,642 A | 6/1988 | Silva et al. | |
| 4,757,022 A | 7/1988 | Shults et al. | |
| 4,768,229 A | 8/1988 | Benjamin et al. | |
| 4,779,199 A | 10/1988 | Yoneda et al. | |
| 4,796,639 A | 1/1989 | Snow et al. | |
| 4,799,199 A | 1/1989 | Scales, III et al. | |
| 4,803,625 A | 2/1989 | Fu et al. | |
| 4,835,372 A | 5/1989 | Gombrich et al. | |
| 4,838,275 A | 6/1989 | Lee | |
| 4,858,354 A | 8/1989 | Gettler | |
| 4,858,617 A | 8/1989 | Sanders | |
| 4,897,869 A | 1/1990 | Takahashi | |
| 4,899,839 A | 2/1990 | Dessertine et al. | |
| 4,907,973 A | 3/1990 | Hon | |
| 4,916,441 A | 4/1990 | Gombrich | |
| 4,933,873 A | 6/1990 | Kaufman et al. | |
| 4,950,246 A * | 8/1990 | Muller | 604/154 |
| 4,995,402 A | 2/1991 | Smith et al. | |
| 5,007,429 A | 4/1991 | Treatch et al. | |
| 5,016,172 A | 5/1991 | Dessertine | |
| 5,019,974 A * | 5/1991 | Beckers | 600/316 |
| 5,024,225 A | 6/1991 | Fang | |
| 5,025,374 A | 6/1991 | Roizen et al. | |
| 5,033,474 A | 7/1991 | Varelis et al. | |
| 5,034,807 A | 7/1991 | Von Kohorn | |
| 5,036,852 A | 8/1991 | Leishman | |
| 5,050,612 A | 9/1991 | Matsumura | |
| 5,056,059 A | 10/1991 | Tivig et al. | |
| 5,065,315 A | 11/1991 | Garcia | |
| 5,068,536 A | 11/1991 | Rosenthal | |
| 5,077,476 A | 12/1991 | Rosenthal | |
| 5,095,798 A | 3/1992 | Okada et al. | |
| 5,109,974 A | 5/1992 | Beer et al. | |
| 5,111,817 A | 5/1992 | Clark et al. | |
| 5,120,230 A | 6/1992 | Clark et al. | |
| 5,128,752 A | 7/1992 | Von Kohorn | |
| 5,134,391 A | 7/1992 | Okada | |
| 5,137,028 A | 8/1992 | Nishimura | |
| 5,142,358 A | 8/1992 | Jason | |
| 5,142,484 A | 8/1992 | Kaufman et al. | |
| 5,176,502 A | 1/1993 | Sanderson et al. | |
| 5,182,707 A | 1/1993 | Cooper et al. | |
| 5,204,670 A | 4/1993 | Stinton | |
| 5,216,597 A | 6/1993 | Beckers | |
| 5,222,020 A | 6/1993 | Takeda | |
| 5,226,431 A | 7/1993 | Bible et al. | |
| 5,227,874 A | 7/1993 | Von Kohorn | |
| 5,249,044 A | 9/1993 | Von Kohorn | |
| 5,261,401 A | 11/1993 | Baker et al. | |
| 5,262,943 A | 11/1993 | Thibado et al. | |
| 5,277,197 A | 1/1994 | Church et al. | |
| 5,299,121 A | 3/1994 | Brill et al. | |
| 5,307,263 A | 4/1994 | Brown | |
| 5,316,008 A | 5/1994 | Suga et al. | |
| 5,329,459 A | 7/1994 | Kaufman et al. | |
| 5,329,608 A | 7/1994 | Bocchieri et al. | |
| 5,331,549 A | 7/1994 | Crawford, Jr. | |
| 5,331,555 A | 7/1994 | Hashimoto et al. | |
| 5,336,245 A | 8/1994 | Adams et al. | |
| 5,339,821 A | 8/1994 | Fujimoto | |
| 5,341,291 A | 8/1994 | Roizen et al. | |
| 5,344,324 A | 9/1994 | O'Donnell et al. | |
| 5,357,427 A | 10/1994 | Langen et al. | |
| 5,359,509 A | 10/1994 | Little et al. | |
| 5,366,896 A | 11/1994 | Margrey et al. | |
| 5,377,100 A | 12/1994 | Pope et al. | |
| 5,377,258 A | 12/1994 | Bro | |
| 5,381,138 A | 1/1995 | Stair et al. | |
| 5,390,238 A | 2/1995 | Kirk et al. | |
| 5,399,821 A | 3/1995 | Inagaki et al. | |
| 5,410,471 A | 4/1995 | Alyfuku et al. | |
| 5,434,611 A | 7/1995 | Tamura | |
| 5,441,047 A | 8/1995 | David et al. | |
| 5,454,721 A | 10/1995 | Kuch | |
| 5,454,722 A | 10/1995 | Holland et al. | |
| 5,465,082 A | 11/1995 | Chaco | |
| 5,467,269 A | 11/1995 | Flaten | |
| 5,471,039 A | 11/1995 | Irwin, Jr. et al. | |
| 5,483,276 A | 1/1996 | Brooks et al. | |
| 5,488,423 A | 1/1996 | Walkingshaw | |
| 5,501,231 A | 3/1996 | Kaish | |
| 5,502,636 A | 3/1996 | Clarke | |
| 5,504,519 A | 4/1996 | Remillard | |
| 5,515,303 A * | 5/1996 | Cargin et al. | 361/679.32 |
| 5,517,405 A | 5/1996 | McAndrew et al. | |
| 5,524,637 A | 6/1996 | Erickson | |
| 5,527,239 A | 6/1996 | Abbondanza | |
| 5,542,420 A | 8/1996 | Goldman et al. | |
| 5,544,649 A | 8/1996 | David et al. | |
| 5,549,117 A | 8/1996 | Tacklind et al. | |
| 5,550,575 A | 8/1996 | West et al. | |
| 5,553,609 A | 9/1996 | Chen et al. | |
| 5,558,638 A | 9/1996 | Evers et al. | |
| 5,569,212 A | 10/1996 | Brown et al. | |
| 5,572,421 A * | 11/1996 | Altman et al. | 705/3 |
| 5,574,828 A | 11/1996 | Hayward et al. | |
| 5,576,952 A | 11/1996 | Stutman et al. | |
| 5,583,758 A | 12/1996 | McIlroy et al. | |
| 5,594,637 A | 1/1997 | Eisenberg et al. | |
| 5,596,994 A | 1/1997 | Bro | |
| 5,597,307 A | 1/1997 | Redford et al. | |
| 5,601,435 A | 2/1997 | Quy | |
| 5,619,991 A | 4/1997 | Sloane | |
| 5,624,265 A | 4/1997 | Redford et al. | |
| 5,628,309 A | 5/1997 | Brown | |
| 5,631,844 A | 5/1997 | Margrey et al. | |
| 5,633,910 A | 5/1997 | Cohen | |
| 5,642,731 A | 7/1997 | Kehr | |
| 5,642,936 A | 7/1997 | Evans | |
| 5,659,793 A | 8/1997 | Escobar et al. | |
| 5,664,228 A | 9/1997 | Mital | |
| 5,670,711 A | 9/1997 | Detournay et al. | |
| 5,675,635 A | 10/1997 | Vos et al. | |
| 5,678,562 A | 10/1997 | Sellers | |
| 5,678,571 A | 10/1997 | Brown | |
| 5,680,590 A | 10/1997 | Parti | |
| 5,687,322 A | 11/1997 | Deaton et al. | |
| 5,687,717 A | 11/1997 | Halpern et al. | |
| 5,704,366 A | 1/1998 | Tacklind et al. | |
| 5,704,902 A | 1/1998 | Vandenbelt et al. | |
| 5,711,297 A | 1/1998 | Iliff | |
| 5,715,451 A | 2/1998 | Marlin | |
| 5,717,913 A | 2/1998 | Driscoll | |
| 5,720,733 A | 2/1998 | Brown | |
| 5,722,418 A | 3/1998 | Bro | |
| 5,727,153 A | 3/1998 | Powell | |
| 5,732,709 A | 3/1998 | Tacklind et al. | |
| 5,752,234 A | 5/1998 | Withers | |
| 5,752,235 A | 5/1998 | Kehr et al. | |
| 5,760,771 A | 6/1998 | Blonder et al. | |
| 5,772,585 A | 6/1998 | Lavin et al. | |
| 5,782,814 A | 7/1998 | Brown et al. | |
| 5,785,650 A | 7/1998 | Akasaka et al. | |
| 5,791,342 A | 8/1998 | Woodard | |
| 5,792,117 A | 8/1998 | Brown | |
| 5,793,969 A | 8/1998 | Kamentsky et al. | |
| 5,796,393 A | 8/1998 | MacNaughton et al. | |
| 5,800,458 A | 9/1998 | Wingrove | |
| 5,802,494 A | 9/1998 | Kuno | |
| 5,810,747 A | 9/1998 | Brudny et al. | |

| | | |
|---|---|---|
| 5,812,983 A | 9/1998 | Kumagai |
| 5,819,735 A | 10/1998 | Mansfield et al. |
| 5,822,544 A | 10/1998 | Chaco et al. |
| 5,822,715 A | 10/1998 | Worthington et al. |
| 5,825,283 A | 10/1998 | Camhi |
| 5,827,180 A | 10/1998 | Goodman |
| 5,828,943 A | 10/1998 | Brown |
| 5,832,448 A | 11/1998 | Brown |
| 5,835,896 A | 11/1998 | Fisher et al. |
| 5,836,304 A | 11/1998 | Kellinger et al. |
| 5,842,976 A | 12/1998 | Williamson |
| 5,868,669 A | 2/1999 | Iliff |
| 5,875,432 A | 2/1999 | Sehr |
| 5,879,163 A | 3/1999 | Brown et al. |
| 5,887,133 A | 3/1999 | Brown et al. |
| 5,893,077 A | 4/1999 | Griffin |
| 5,893,098 A | 4/1999 | Peters et al. |
| 5,897,493 A | 4/1999 | Brown |
| 5,899,855 A | 5/1999 | Brown |
| 5,911,687 A | 6/1999 | Sato et al. |
| 5,913,310 A | 6/1999 | Brown |
| 5,918,603 A | 7/1999 | Brown |
| 5,920,477 A | 7/1999 | Hoffberg et al. |
| 5,933,136 A | 8/1999 | Brown |
| 5,935,060 A | 8/1999 | Iliff |
| 5,940,801 A | 8/1999 | Brown |
| 5,945,651 A | 8/1999 | Chorosinski et al. |
| 5,950,632 A | 9/1999 | Reber et al. |
| 5,951,300 A | 9/1999 | Brown |
| 5,954,641 A | 9/1999 | Kehr et al. |
| 5,956,501 A | 9/1999 | Brown |
| 5,960,403 A | 9/1999 | Brown |
| 5,961,446 A | 10/1999 | Beller et al. |
| 5,983,217 A | 11/1999 | Khosravi-Sichani et al. |
| 5,985,559 A | 11/1999 | Brown |
| 5,987,471 A | 11/1999 | Bodine et al. |
| 5,995,969 A | 11/1999 | Lee et al. |
| 5,997,476 A | 12/1999 | Brown |
| 6,001,065 A | 12/1999 | DeVito |
| 6,022,315 A | 2/2000 | Iliff |
| 6,022,615 A | 2/2000 | Rettenbacher |
| 6,029,138 A | 2/2000 | Khorasani et al. |
| 6,032,119 A | 2/2000 | Brown et al. |
| 6,046,761 A | 4/2000 | Echerer |
| 6,049,794 A | 4/2000 | Jacobs et al. |
| 6,050,940 A | 4/2000 | Braun et al. |
| 6,055,314 A | 4/2000 | Spies et al. |
| 6,055,487 A | 4/2000 | Margery et al. |
| 6,055,506 A | 4/2000 | Frasca, Jr. |
| 6,057,758 A | 5/2000 | Dempsey et al. |
| 6,101,478 A | 8/2000 | Brown |
| 6,110,148 A | 8/2000 | Brown et al. |
| 6,138,145 A | 10/2000 | Kawanaka |
| 6,144,837 A | 11/2000 | Quy |
| 6,151,581 A * | 11/2000 | Kraftson et al. ........... 705/3 |
| 6,151,586 A | 11/2000 | Brown |
| 6,161,095 A | 12/2000 | Brown |
| 6,167,362 A | 12/2000 | Brown et al. |
| 6,168,563 B1 | 1/2001 | Brown |
| 6,177,940 B1 | 1/2001 | Bond et al. |
| 6,186,145 B1 | 2/2001 | Brown |
| 6,189,029 B1 | 2/2001 | Fuerst |
| 6,196,970 B1 | 3/2001 | Brown |
| 6,210,272 B1 | 4/2001 | Brown |
| 6,233,539 B1 | 5/2001 | Brown |
| 6,240,393 B1 | 5/2001 | Brown |
| 6,246,992 B1 | 6/2001 | Brown |
| 6,248,065 B1 | 6/2001 | Brown |
| 6,260,022 B1 | 7/2001 | Brown |
| 6,270,455 B1 | 8/2001 | Brown |
| 6,270,456 B1 | 8/2001 | Iliff |
| 6,330,426 B2 | 12/2001 | Brown |
| 6,334,778 B1 | 1/2002 | Brown |
| 6,368,273 B1 | 4/2002 | Brown |
| 6,375,469 B1 | 4/2002 | Brown |
| 6,381,577 B1 | 4/2002 | Brown |
| 6,849,045 B2 | 2/2005 | Iliff |
| 6,968,375 B1 | 11/2005 | Brown |
| 7,167,818 B2 | 1/2007 | Brown |
| 7,168,818 B1 | 1/2007 | Schnell |
| 7,252,636 B2 | 8/2007 | Brown |
| 7,305,348 B1 | 12/2007 | Brown |

FOREIGN PATENT DOCUMENTS

| | | |
|---|---|---|
| EP | 0286456 | 10/1988 |
| EP | 0320749 | 6/1989 |
| EP | 370599 | 5/1990 |
| EP | 0353046 | 10/1990 |
| EP | 0461910 | 12/1991 |
| EP | 508912 | 10/1992 |
| EP | 526166 | 2/1993 |
| EP | 0558975 | 9/1993 |
| EP | 0-653-718 A2 | 5/1995 |
| EP | 676709 | 10/1995 |
| EP | 680727 | 11/1995 |
| EP | 761160 | 3/1997 |
| EP | 0813155 | 12/1997 |
| GB | 2218831 | 11/1989 |
| GB | 2225637 | 6/1990 |
| JP | 5400-5785 | 1/1979 |
| JP | 54-146633 | 11/1979 |
| JP | 62-226278 | 10/1987 |
| JP | 5-155024 | 6/1993 |
| JP | 5-266002 | 10/1993 |
| WO | WO-85-01667 | 4/1985 |
| WO | WO-90-00367 | 1/1990 |
| WO | WO-91-09374 | 6/1991 |
| WO | WO-93-01489 | 1/1993 |
| WO | WO-93-02622 | 2/1993 |
| WO | WO-94-16774 | 8/1994 |
| WO | WO-95-09386 | 4/1995 |
| WO | WO-95-20199 | 7/1995 |
| WO | WO-95-22131 | 8/1995 |
| WO | WO-95-29447 | 11/1995 |
| WO | WO-96-07908 | 3/1996 |
| WO | WO-96-25877 | 8/1996 |
| WO | WO-96-36923 | 11/1996 |
| WO | WO-97-08605 | 3/1997 |
| WO | WO-97-12544 | 4/1997 |
| WO | WO-97-37738 | 10/1997 |
| WO | WO-98-16895 | 4/1998 |

OTHER PUBLICATIONS

Moore, New Applications Break Through Storage Boundaries, Computer Technology Review, (Oct. 1999), vol. 19, No. 10 p. 1.

Bruce, Health Hero Network CEO, CNNfn, Digital Jam, (Dec. 1, 1999), 3.

Digital Doggie; retrieved from URL http://www.virtualpet.com/vp/farm/gigapet/ddoggie.htm Apr. 23, 2000.

Giga Farm; retrieved from URL http://www.virtualpet.com/vp/farm/gigapet/gpfarm/gpfarm.htm Apr. 23, 2000.

Nano Baby Instructions; retrieved from file://C:\My Documents\Nano Baby Instructions.htm Apr. 23, 2000.

Nano Fighter Pets; retrieved from URL http://www.virtualpet.com/vp/farm/nano/nfighter.htm Apr. 23, 2000.

Playmates Toys deals knockout blow to virtual pet competitors with introduction of Nano FighterÔ For Boys; New Nano Pet Fighting Pet Press Release; retrieved from URL http://www.virtualpet.com/vp/farm/nano/nfightpr.htm Apr. 23, 2000.

Talking Nano Puppy; retrieved from URL http://www.virtualpet.com/vp/farm/nano/talkn/talkn.htm Apr. 23, 2000.

Towards a partnership of care, M2 Presswire, Jun. 14, 2000.

Sep. 24, 2001 09300856_Amendment.

Schenkels, P., Supplementary European Search Report, Application No. EP 97 92 2716, (Mar. 11, 2002).

How Flash Memory Works, Internet printout of URL address: http://www.howstuffworks.com/flash-memory4.htm, (Sep. 28, 2002), 2 pages.

Apr. 21, 2003 09422046_Amendment_with_Affidavit.

Tandy Radio Shack , The description of the Tandy Radio Shack TRS-80 Model 100/102 device available at http://www.old-computuers.com/musuem/computer.asp?c=233, World Wide Web, (Feb. 13, 2004), 1-3.

Jun. 13, 2005 1150145_Amendment.

Mar. 29, 2006 11150145_OA.
Jun. 19, 2006 09237194_Office_Actions_Response.
Jun. 26, 2006 11150145_Amendment.
Aug. 17, 2006 Abbott_Amended_Complaint.
Aug. 17, 2006 Abbott_v_Dexcom_06-514.
Aug. 17, 2006 Request_for_Re-examination_5899855_90008234.
Sep. 21, 2006 09237194_Declation_of_Stephen_Brown_with_Attached_Exhibits_Y_and_Z_thereof.
Sep. 22, 2006 11150145_OA.
Sep. 27, 2006 09422046_Office_Actions_Response.
Oct. 27, 2006 11150145_Amendment.
Jan. 4, 2007 1150145_Amendment.
May 9, 2007 Leapfrog_v_Fisher_Price.
Oct. 29, 2007 Request_for_Re-examination_5899855_90008909.
Nov. 9, 2007 Request_for_Re-examination_7223236_90010053.
Nov. 15, 2007 Request_for_Re-examination_7223236_90010053.
Jan. 18, 2008 Determination_for_Re-examination_7223236_90010053.
Jan. 25, 2008 Dept_of_Health_and_Human_Services_The_Physicians_Guide_Become_publicly_Available.
Jun. 20, 2008 09422046_OA.
Jun. 20, 2008 Alere_First_Supplemental_Response_to_Plaintiff_Interrogatories.
Aug. 1, 2008 Excerpts_from_the_Prosecution_History_for_US_Patent_5899855.
Aug. 1, 2008 Inter_Party_Re-Exam_7223236_95000386.
Aug. 1, 2008 Request_for_Re-examination_5601435_90009237.
Aug. 1, 2008 Request_for_Re-examination_5879163_90009238.
Aug. 1, 2008 Request_for_Re-examination_6151586_90009240.
Aug. 1, 2008 Request_for_Re-examination_7223236_95000386.
Sep. 23, 2008 Request_for_Re-Examination_6368273_90009281.
Dec. 4, 2008 Request_for_Re-Examination_5899855_90009352.
Dec. 10, 2008 Alere_Second_Supplemental_Response_to_Plaintiff_Interrogatories.
Dec. 10, 2008 Alere_Second_Supplemental_Response_to_Plaintiff_Interrogatories_Exhibit_1.
Dec. 10, 2008 Alere_Second_Supplemental_Response_to_Plaintiff_Interrogatories_Exhibit_2.
Dec. 10, 2008 Alere_Second_Supplemental_Response_to_Plaintiff_Interrogatories_Exhibit_3.
Dec. 10, 2008 Alere_Second_Supplemental_Response_to_Plaintiff_Interrogatories_Exhibit_4.
Dec. 10, 2008 Alere_Second_Supplemental_Response_to_Plaintiff_Interrogatories_Exhibit_6.
Dec. 10, 2008 Alere_Second_Supplemental_Response_to_Plaintiff_Interrogatories_Exhibit_7.
Dec. 10, 2008 Alere_Second_Supplemental_Response_to_Plaintiff_Interrogatories_Exhibit_8.
Dec. 10, 2008 Alere_Second_Supplemental_Response_to_Plaintiff_Interrogatories_Exhibit_8A.
Dec. 10, 2008 Alere_Second_Supplemental_Response_to_Plaintiff_Interrogatories_Exhibit_B.
5V Powered Isolated RS-232 Drivers/Receivers Maxim Integrated Products.
Albisser, A.M. Intelligent Instrumentation in Diabetic Management, CRC Critical Reviews in Biomedical Engineering, vol. 17, No. 1, pp. 1-24, 1989.
American_Heritage_Dictionary_pa.
American_Heritage_Dictionary_pe.
Auction Web, http://www.ebay.com.
Bai, Design of home healthcare network, IEEE 1997 pp. 1657-1658.
CD-ROM Mavericks: Proprietary TV-Based Players, Byte Guide to CD-ROM, pp. 100-105.
Results of the world's first on-line auction, http://www.christies.com. Save the earth artrock auction, http://www.commerce.com.save-earth. Auction Web, http://www.ebay.com.
Skolnick et al. Simultaneous Analysis of Multiple Polymorphic Loci Using Amplified Sequence Polymorphisms (ASPs); Genomics. 2: 273-279, 1988.
The_Merriam_Webster_Online_Dictionary_display.
The_Merriam_Webster_Online_Dictionary_graphic.
The_Merriam_Webster_Online_Dictionary_pictorial.
The_Merriam_Webster_Online_Dictionary_symbol.
The_Merriam_Webster_Online_Dictionary_symbolic.
The_Merriam_Webster_Online_Dictionary_Video.
Websters_Dictionary_II_com.
Websters_Dictionary_II_con.
Websters_Dictionary_II_i.
Websters_Dictionary_II_m.
Gardner, et al.; Comprehension and Appreciation of Humorous Material Following Brain Damage; Brain; Sep. 1975; 98(3); pp. 399-412; Dialog: File 153, Acc#02859983. (14 pages).
Mar. 20, 1978 Caprihan, A., et al., A Simple Microcomputer for Biomedical Signal Processing, IECI '78 Annual Conference Proceedings on Industrial Applications of Microprocessors, (Mar. 20, 1978), 18-23.
Nov. 1978 Licklider_Applications_of_information_Networks_Proceedings_of_the_IEEE_vol._66_No._11.
Jan. 1980 Haynes_Geriatrics_How_to_Detect_manage_Low_Patient_Compliance_in_Chronic_Illness.
Haynes_Hypertension_Can_simple_Clinical_measurements_detect_patient_noncompliance.
Kuykendall, V.G., et al., Assessment of Self-Monitored Blood Glucose results Using a Reflectance Meter with Memory and Microcomputer, Symposium on Computer Applications in Medical Care, (Jan. 1981), vol. 70, pp. 98-102.
Soeldner, J. S., Treatment of Diabetes Mellitus by Devices, The American Journal of Medicine, (Jan. 1981), vol. 70, 183-194.
Kennedy et al.; Television Computer Games: A New Look in Performance Testing; Aviat Space Environ Med; Jan. 1982, 53(1); pp. 49-53. (5 pages); Dialog Abstract: File 155, Acc#0353751.
Mule. Rulebook by Electronic Arts, 1983.
Mazzola, et al., Video Diabetes: A Teaching Tool for Children with Insulin-Dependent Diabetes, Proceedings—7th Annual Symposium on Computer Applications in Medical Care; Washington, DC; Dialog:, (Oct. 1983), File 8, Acc# 01624462.
Adilman; Videogames: Knowing the Score; Creative Computing; v9; p. 224(5); Dec. 1983; Dialog: File 148, Acc# 01891055.
Gauntlet (for PC) rulebook by Mindscape Inc. (Gauntlet by Apple);1985.
Mims; Psychological Testing; Computers & Electronics; v23; p. 22(6); Feb. 1985; Dialog: File 47, Acc# 2654858.
1986 Physicians_Guide_Using_the_Health_Buddy_System.
Thompson and Vandenberg, Clinical Biochemistry (1986) 19:255-261.
Oct. 19, 1986 Thompson_In_Vivo_Probes.
Jun. 2, 1987 U.S. Appl. No. 07/096,998 Lee_Amendment.
Hunter, Technological Advances in Bedside Monitoring: Biosensors, Archives and Laboratory Medicine, (Jul. 1987), pp. 633-636.
Roberts; Diabetes and Stress: A Type A Connection?, Psychology Today, (Jul. 1987), v. 21; pp. 22(1); Dialog: File 149, Acc# 05038381.
1988 Hughes_Bedside_Terminals_Clinicom_MD.
Leyerle, Beverly J., et al., The PDMS as a Focal Point for Distributed Patient Data, International Journal of Clinical Monitoring and Computing, (1988), vol. 5, pp. 155-161.
Yoshizawa, Daisuke, et al., The Development of a Data Processing System with Personal Computer MSX Standard System for Flow Injection Analysis, Journal of Flow Injection Analysis, (1988), V.5, No. 2, pp. 101-110.
Aug. 10, 1988 U.S. Appl. No. 06/879,900 Fu_Amendment.
Douglas, A.S., et al., Hand-Held Glucose Monitor and Recorder, Proceedings of the Annual International Conference of the IEEE Engineering in Medicine and Biology Society, New Orleans, LA, (Nov. 1988), pp. 747-748.
Velho et. al., Biomed. Biochim. Acta (1989) 48(11/12):957:964.
May 1989 Paperny_Adolescent_Pregnancy_Prevention_by_Health_Education_Computer_Games_Computer_Assisted_Instruction.
Oct. 12, 1989 Diabcare Flyer Boehringer Mannheim HH101661-HH101668.
1990 Matthews_et_al_BMJ_Analysis_of_serial_measurement_in_medical_research.

Miles, Laughton E., A Portable Microcomputer for Long-Term Physiological Monitoring in the Home and Work Environment, Medical Monitoring in the Home and Work Environment, (1990), pp. 47-57.

Pfeiffer, E. F., The Glucose Sensor: The Missing Link in Diabetes Therapy, Hormone and Metabolic Research, (1990), vol. 24m Suppl. pp. 154-164.

Schrezenmeir, J. et al., Computer Assisted Insulin Dosage Adjustment—Perspective for Diabetes Control, Hormone and Metabolic Research, Supplement Series, (1990), vol. 24, pp. 116-123.

Shandle, Jack, Who Will Dominate the Desktop in the 90's?, , Electronics, Feb. 1990, pp. 48-50. (3 pages).

1991 Diabcare User Manual HH007288-HH007331.

Fabietti, P.G., et al., Wearable System for Acquisition, Processing and Storage of the Signal from Amperometric Glucose Sensors, The International Journal of Artificial Organs, (1991), vol. 14, No. 3, pp. 175-178.

Latman, N.S., Evaluation of Electronic, Digital Blood Glucose Monitors, Biomedical Instrumentation and Technology, (1991), vol. 25, No. 1, 43-49.

Vallera, D. A., et al., Accuracy of Portable Blood Glucose Monitoring, American Journal of Clinical Pathology, (1991), vol. 95, No. 2, pp. 247-252.

Billiard, A., et al. Telematic Transmission of Computerized Blood Glucose Profiles for IDDm Patients, Diabetes Care, (Feb. 1991), vol. 14, No. 2, pp. 130-134.

Jul. 23, 1991 Dept_of_Health_and_Human_Services_the_Physician_Guide_from_the_K864318_510K.

Bruce, et al., The Effects of Sympathetic Nervous System Activation and Psychological Stress . . . ; Diabetologia; 35(9); 1992; 835-843; Dialog: File 5, Acc#9629427. (9 pages).

1992 Durant Medicine and Science in Sports and Exercise 24(2)265-271.

Jimison et al., Patient-Specific explanation in models of chronic disease, Revised Feb. 1992 Artificial Intelligence in Medicine 4 (1992) 191-205.

Bower, Brain Clues to Energy-efficient Learning, Science News, (Apr. 1992), v. 141; p. 215(1); Dialog: File 647, Acct# 12123949.

Schement, An Intelligent Controller for Neurophysiological Experiments, Proceeding of the Annual Symposium on Computer Based Medical Systems, Durham, Jun. 14-17, 1992, p. 528, line 1—p. 529, line 21.

Frieberger, Paul, Video Game Takes on Diabetes Superhero 'Captain Novolin' Offers Treatment Tips, San Francisco Examiner, (Jun. 26, 1992), Fourth Edition, Business Section B1.

Oct. 1992 McCullagh, PJ et al, Computerized paradigms for eliciting the contingent negative variation event-related potential, Proceedings of the Annual International Conference of the Engineering in Medicine & Biology Society, IEEE, Conf. 14, p. 2481-2483.

Hauser, et al., Will Computers Replace or Complement the Diabetes Educator?, The Medical Journal of Australia, (Oct. 5, 1992), vol. 157, 489-491.

Nov. 13, 1992 Letter.

Brunetti, P., et al., A Simulation Study on a Self-Turning Portable Controller of Blood Glucose, The International Journal of Artificial Organs, (1993), vol. 16, No. 16, pp. 51-57.

1993 Camit S Manual v3.00.

Introducing the Next Generation of About Your Diabetes, U.S. Pharmacopical Convention and American Diabetes Association, (1993).

Poitout, A Glucose Monitoring System for On Line Estimation in Man of Blood Glucose Concentration Using a Miniaturized Glucose Sensor Implanted in the Subcutaneous Tissue and a Wearable Control Unit, Diabetologia, (1993), vol. 36, pp. 658-663.

Rose, V. L., et al., Decentralized Testing for Prothrombin Time and Activated Partial Thromboplastin Time Using a Dry Chemistry Portable Analyser, Archives of Pathology and Laboratory Medicine, (Jun. 1993), vol. 117, pp. 611-617.

Furnham, et al; Measuring Locus of Control: a Critique of General Children's Health- and Work-related Locus of Control Questionnaires; British Journal of Psychology; v84 n4; p. 443(37); Nov. 1993; Dialog: File 88, Acc# 14903135.

Kaufman, Steven, B., The Learning Game, Nation's Business, (Nov. 1993).

Franklin; Proposed Auction Rules for PCS: The FCC Plans to Use Competitive Bidding, but Exact Procedures are Undefined; Cellular Business; v10 n13; p. 18(2); Dec. 1993; Dialog: File 148, Acc#06787310.

Anonymous, Health Hero Network, Inc. Receives First-Ever FDA Clearance for Connecting Medical Devices to Internet, PR Newswire, (Dec. 2, 1993), 3 pages.

Makikawa, M., et al., Microprocessor-Based Memory Device for Ambulatory Heart Rate and Physical Activity Recording, Methods of Information in Medicine, (1994), vol. 33, No. 1, pp. 94-96.

Potter, David, Fundamentals of PC-Based Data Acquisition, Sensors, (Feb. 1994), pp. 12-20.

Horio, Hiroyuki, et al., Clinical Telecommunication Network System for Home Monitoring, Medical & Biological Engineering & Computing, (Mar. 1994), vol. 32, 227-230.

Howey, et al., A Rapidly Absorbed Analogue of Human Insulin; Diabetes, vol. 43, Mar. 1994, pp. 396-402. (7 pages).

Finston, Parent + Teacher = Healthy Child, Diabetes Forecast, (Apr. 1994), v47 n9; p. 26(5); Dialog: file 149, Acc# 15804228.

May 1994 Szolovits_Guardian_Angel_Patient_Centered_Health_Information_Systems.

Jul. 1994 Genesereth_Software_Agents.

O'Donnell; Alan's At It Again; Bond Buyer; v309 n29448; p. 1(3); Jul. 21, 1994; Dialog: File 148, Acc#07478152.

Valla, et al., A Structured Pictorial Questionnaire to Assess DSM-III-R-based Diagnosis in Children (6-11 years); Journal of Abnormal Child Psychology; v22 n4; p. 403(21); Aug. 1994; Dialog: File 88, Acc# 15759542.

Shults, Marc C., et al., A Telemetry-Instrumentation System for Monitoring Multiple Subcutaneously Implanted Glucose Sensors, IEEE Transactions on Biomedical Engineering, (Oct. 1994), vol. 41, No. 10, pp. 937-942.

Wyatt, J. C., Clinical Data Systems, Part 2: Components and Techniques, Lancet, (Dec. 1994), vol. 344, No. 8937, pp. 1609-1614.

Hauben, Jay R., A Brief History of the Cleveland Free-Net, available at http://www.ais.org/~irh/acn7-1.a09.html, (1995) pp. 1-4.

Gordon; Auctions Become High Tech; Dealer Business; v29 n7; p. 21(4); Mar. 1995; Dialog: File 148, Acc#07862519.

ONSALE Onsale Brings Thrill of Auctions and Bargain Hunting Online; Unique Internet retail service debuts with week-long charity auction for The Computer Museum in Boston, May 24, 1995; Dialog Abstract: File 610, Acc#0489267.

Onsale Joins Fray as Online Shopping Picks Up Speed: Internet Booms; Computer Reseller News; Jun. 5, 1995; p. 73; DIALOG: File 16, Acc#05649796.

Aug. 10, 1995 Lai_Abstraction_Models_at_System_Level_for_Networked_Interactive_Multimedia_Scripting.

Sep. 1, 1995 Lunt_The_Smart_Cards_Are_Here.

Cathay Pacific Airways-USA receives more than 1,300 bids during first five days of CyberAuction; Business Wire, Oct. 18, 1995, p. 10181119.

Seigmann;Nowhere to Go but Up; PC Week; v12 n42, p. A5(1); Oct. 23, 1995; DIALOG: File 148, Acc#08222496.

Meissner, et al., Building an Integrated Clinical and Research Network, Proceedings of the SPIE, (Oct. 24, 1995), vol. 2618, p. 92-99.

Antique Collector , Putting the Lot on the Net, vol. 66, Issue 9, p. 26, Downloaded from Corporate Resource Net, Nov./Dec. 1995.

Nov. 1995 Hoffman_General_Purpose_Telemetry_for_Analog_Biomedical_Signals.

Edelson; Fashion Reevaluates Flickering Fortunes of TV Home Shopping; WWD; v170 n87; p. 1(3); Nov. 8, 1995; DIALOG: File 148, Acc#08289119.

RO_AUCTION Auctioneers Property Database System and RO_AUCTION Auctioneers Accounting System; RO-AUCTION features; Dec. 4, 1995.

Theme Hospital, product review 1996 [retrieved Apr. 21, 2000], Retrieved from.

Williams_Motivational_Predictors_of_Weight_Loss.

Lachnit, Carroll, Hawkin's Online Auction, Photo District News, vol. 16, Issue 1, p. 18, Jan. 1996.

Cheng, Joe H., PCT Search Report, (Jan. 11, 1996).

Luebke, Cathy, Barrett-Jackson Auction Turns High-Tech, Business Journal, vol. 16, Issue 12, pp. 11, Jan. 19, 1996.

Brenman et al.; Interaction of Nitric Oxide Synthase with the Postsynaptic Density Protein PSD-95 and a1-Syntrophin Mediated by PDZ Domains; Cell; vol. 84, pp. 757-767, Mar. 8, 1996; Ref: XP-002104701.

Mar. 8, 1996 Cathay Pacific Airways-USA to Hold First-Ever Internet CyberAuction; CyberTravelers Can Bid for 50 Business Class Round Trips to Hong Kong—No Minimum Bid; Business Wire; p9261084; Sep. 26, 1995; DIALOG: File 148, Acc#08167091.

Voelker, Rebecca, Shoe Leather Therapy is Gaining on TB, Jama, (Mar. 13, 1996), vol. 275, 743.

Spitzer et al.; The moderating effect of age on self-care; Western Journal of Nursing Research, v18, n2, p. 136(13), Apr. 1996.

Marx, Wendy, More than just the Scores: ESPNET SportsZone is a model for expanding brand names online, InformationWeek, n576 p. 61(2), Apr. 22, 1996.

Jones, Chris, Microsoft readies DocObject; technology will allow document editing in Web browsers, InfoWorld, v18 n18 p. 48(1), Apr. 29, 1996.

Hutheesing, Nikhil, An on-line gamble, Forbes, v157 n10 p. 288(1), May 20, 1996.

Jul. 12, 1996 Iliff U.S. Appl. No. 60/021,614.

United Healthcare's OPTUM Division goes online to better health by announcing a unique internet application. PR Newswire, p0801MNTH004. Aug. 1, 1996.

Seybold—New Horizons teams with Duke, Real Media; The Seybold Report on Desktop Publishing, v10 n12 p. 24(1), Aug. 12, 1996.

Research project launched to improve health of America's communities; new Disney community in Florida is focus of program. Business Wire, p10011142. Oct. 1, 1996.

AdOptimizer—Ad Management Software for Websites, Newsbytes, pNEW10040041, Oct. 4, 1996.

Telemedicine Provides Two-Way Computer Link for Parents of Very Premature Infants. PR Newswire. p1007NEM034. Oct. 7, 1996.

Jaffrey et al.; PIN: An Associated Protein Inhibitor of Neuronal Nitric Oxide Synthase; Science; vol. 274; Nov. 1, 1996; Ref: XP 002050141.

DigiPet Instruction Manual, 1997.

Future of the Virtual Pet Industry, 1997 [retrieved on Apr. 23, 2000], Retrieved from.

Giga Pets, 1997 [retrieved on Apr. 23, 2000], Retrieved from.

Guiffrida, et al., Should We Pay the Patient? Review of Financial Incentives to enhance Patient Compliance:, Biomedical Journal, (1997), vol. 315, pp. 703-707.

Kauffmann, et al., Epidemiological Study of the Genetics and Environment of Asthma, Bronchial Hyperresponsiveness and Atrophy, Am. J. Respir. Crit. Care Med., (1997), vol. 156, pp. S123-S129.

Marsh, David G. Approaches Toward the Genetic Analysis of Complex Traits Asthma and Atrophy, Am. J. Respir.Crit.Care Med., (1997), vol. 156, pp. S-133-S138.

Martinez, Fernando D., Complexities of the Genetics of Asthma, Am.J. Respir. Crit. Care Med., (1997), vol. 156, pp. S117-S122.

Nano Page, 1997 [retrieved on Apr. 23, 2000], Retrieved from.

Octhigotchi Instruction Manual, 1997. Dino-Kun Instruction Manual, 1997.

Polson, Gary Recent Developments and Trends in Keychain Virtual Pets, 1997 [retrieved on Apr. 23, 2000], Retrieved from.

Schork, Nicholas J., Genetics of Complex Disease, Am.J.Respir. Crit. Care Me., (1997), vol. 156, pp. S103-S109.

Tamagotchi, 1997 [retrieved on Apr. 23, 2000], Retrieved from.

Virtual Pet Product Reviews, 1997 [retrieved on Apr. 23, 2000], Retrieved from.

Reis, H, Telemedicine: Transmitting Expertise to the Point of Care Toward an Electronic Patient Record; '97, Nashville, TN, Apr. 27-May 3, 1997, pp. 248-256, v. 3.

Lacyk, John, PCT Search Report, (Jun. 12, 1997).

Nov. 18, 1997 Playmates Toys leads Americas virtual pet craze into its next generation by introducting talking Nano Pals; Talking Nano Pet Press Release; retrieved from URL http://www.virtualpet.com/vp/farm/nano/talkn/tnpress.htm on Apr. 23, 2000.

Blood Glucose Monitors, Portable Health Device, (1998), vol. 17(9), pp. 253-271.

Virtual Tomagutchi, 1998 [retrieved Apr. 23, 2000], Retrieved from.

Fox, Not My Type: Type B Behavior, Type I Diabetes Plus Stress Equals Blood Sugar Blues, Health, (Mar. 1998), v20 n3; pp. 22(1); Dialog: File 149, Acc# 06397959.

EP European Search Report, From 6858P005EP, (Mar. 27, 1998).

Central Fetal Monitoring Systems with Optical Disk Storage, New Technology Brief, (Nov./Dec. 1998), vol. 2, No. 6, pp. 249-251.

Updike, Stuart J., et al., Laboratory Evaluation of New Reusable Blood Glucose Sensor, Diabetes Care, (Nov./Dec. 1998), vol. 11, No. 10, pp. 801-807.

Definition_of_Client_Server_from_PCMAG_COM.

Oct. 30, 1995 Mortorala_introduces_PCMCIA28.8_Modem.

Aug. 1, 2008 Reguest_for_Re-examination_6161095_90009239.

Dec. 10, 2008 Alere_Second_Supplemental_Response_to_Plaintiff_Interrogatories_Exhibit_5.

Dec. 10, 2008 Alere_Second_Supplemental_Response_to_Plaintiff_Interrogatories_Exhibit_9.

* cited by examiner

US 8,032,399 B2

TREATMENT REGIMEN COMPLIANCE AND EFFICACY WITH FEEDBACK

RELATED APPLICATIONS

This application is a continuation of application Ser. No. 10/233,296, filed Aug. 30, 2002, now U.S. Pat. No. 7,970,620 which is a continuation in-part of application Ser. No. 09/304,477, filed May 3, 1999, now U.S. Pat. No. 6,189,910. All of the above-identified applications are incorporated herein by reference in their entirety. This application is also a Continuation application of Ser. No. 11/845,317, filed Aug. 27, 2007, now U.S. Pat. No. 8,015,033 which is a Continuation-in-Part of U.S. Ser. No. 09/237,194 filed on Jan. 26, 1999, which is a Continuation of U.S. Ser. No. 08/481,925 filed on Jun. 7, 1995 of U.S. Pat. No. 5,899,855 issued on May 4, 1999, which is a Continuation of U.S. Ser. No. 08/233,397 filed on Apr. 26, 1994 now abandoned.

BACKGROUND OF THE INVENTION

1. Field of the Invention

This invention relates to interaction with a community of individuals, relating to treatment regimen compliance and efficacy, including supply and use of pharmaceuticals.

2. Related Art

When medical personnel prescribe treatment regimens for patients or "patients" undertake non-prescription treatment regimens (whether such regimens are prescribed or undertaken for medication, physical therapy, psychological therapy, self-improvement, or other purposes), a problem can arise in assuring that the patients comply with the requirements of the treatment regimen. For example, some patients are disorganized, forgetful, or simply unwilling to comply. When the treatment regimen has potential side effects, or when the treatment regimen is to be followed under stated conditions (for example: taking medicine with meals, not with alcohol, or in the evening), patient compliance can be relatively reduced even further. When the treatment regimen is relatively complex, some patients are even unable or unwilling to manage that treatment regimen.

Known methods for monitoring and controlling treatment regimens are relatively costly and limited in capability. Some known methods are described in the following patents:

U.S. Pat. No. 5,408,443, "Programmable Medication Dispensing System," issued Apr. 18, 1995 in the name of Edward D. Weinberger.

U.S. Pat. No. 5,642,731, "Method of and Apparatus for Monitoring the Management of Disease," issued Jul. 1, 1997 in the name of Bruce A. Kehr.

U.S. Pat. No. 5,752,235, "Electronic Medication Monitoring and Dispensing Method," issued May 12, 1998 in the name of Bruce A. Kehr, et al.

While these known methods generally achieve the goal of monitoring and controlling a treatment regimen, particularly a medication regimen, they suffer from several drawbacks and limitations.

First, there is a need to provide a portable system to monitor and encourage compliance, and facilitate data collection, so that patients are restricted as little as possible regarding their activities and movements.

Second, there is a need to determine if patients are actually complying with treatment regimens at times when the patients are relatively remote to client devices for the system. Known methods do not provide adequate feedback to determine whether patients are complying with the treatment regimen unless they remain relatively local to client devices.

Third, there is a need to determine whether treatment regimens have the desired and intended effects. Known methods do not provide adequate feedback to determine whether treatment regimens are effective, or whether patients are suffering any untoward side effects. Using known methods, medical personnel must generally wait for patients to complain, or for medical tests to show, that prescribed treatment regimens are inadequate or are producing side effects. Similarly, using known methods, patients undertaking non-prescribed treatment regimens generally do not have effective or convenient systems to monitor and record whether non-prescribed treatment regimens are producing intended results.

Fourth, there is a need to inform patients to follow treatment regimens, particularly when patients are forgetful or treatment regimens are complex. Although known methods do include reminders to patients, it would be advantageous to tailor those reminders to patients' actual compliance history (thus, providing fewer reminders when they are relatively less necessary and more reminders when they are relatively more necessary).

Fifth, there is a need to leverage expert knowledge to improve response to feedback from patients, and to reduce the time and expense required for medical personnel to individually monitor, evaluate and modify treatment regimens.

Sixth, there is a need to broaden application of reminder and expert knowledge leveraging systems beyond medication regimens, to include physical, psychological, self-improvement and other treatment regimens.

Accordingly, it would be advantageous to provide a portable device that can be coupled and uncoupled to a communication system with feedback to monitor patient compliance with, and effectiveness of, treatment regimens, so that input from patients regarding treatment regimens can be recorded, reviewed, analyzed and otherwise generally acted upon. Medical personnel and/or patients can thus (1) monitor compliance with treatment regimens, (2) monitor effectiveness or side effects of treatment regimens, (3) remind patients no more than necessary, and (4) possibly alter treatment regimens in response to feedback from patients. These advantages are achieved in embodiments of the invention in which a portable device is intermittently coupled to a client device in a client-server system, the patient enters information to the portable device about following the treatment regimen while the portable device is uncoupled, and medical personnel or the patient can receive that information and possibly alter the behavior of the portable device when the portable device is re-coupled to the system.

SUMMARY OF THE INVENTION

The invention provides a method and system for interaction with a community of individuals, relating to compliance with and effectiveness of treatment regimens, including supply and use of pharmaceuticals, using a protocol or other intelligent message which acts in place of a service provider and which is capable of collecting or imparting information to patients in place thereof. Individuals interact with the protocol or intelligent message to provide assistance in all aspects of treatment regimen compliance, data collection, supply or delivery, review and modification. These aspects can include (1) reminders regarding compliance with a selected treatment regimen for medication, physical therapy, psychological therapy, self-improvement, or some combination thereof, (2) data collection of facts regarding patient compliance, symptomology, possible drug interactions or side effects of medication if required by the treatment regimen, and other facts relevant to evaluation and possible modification of the treatment regimen; (3) networked integration with workstations for medical professionals to automate approvals and modifications, and refills and delivery of medication if required by the treatment regimen.

A system includes a set of client devices and a server device. A service provider determines a treatment regimen for selected patients, determines a protocol to be followed by the client devices to assist the patient in complying with that treatment regimen [in assisting with that medication regimen] and to maximize effectiveness of treatment, and sends that protocol to the server device. The server device can update (responsive to the protocol) selected instructions at the client devices, and can receive (responsive to selected instructions) information from the client devices regarding their associated patients.

In a first preferred embodiment, a client device, located locally to a patient, couples to a portable device (such as a cellular telephone, pager, "Palm Pilot" or other handheld computer, or watch), capable of being carried away by the patient to locations relatively remote from the client device. The client device can interact with the portable device: (1) to provide the portable device with the capability of reminding the patient regarding the treatment regimen, or (2) to provide the portable device with the capability of further data collection regarding the patient. The client device can interact with the portable device using a docking connection, an infrared connection, a radio-frequency connection, a plug-in connection, or another suitable connection.

DETAILED DESCRIPTION OF THE PREFERRED EMBODIMENT

In the following description, a preferred embodiment of the invention is described with regard to preferred process steps and data structures. Embodiments of the invention can be implemented using general purpose processors or special purpose processors operating under program control, or other circuits, adapted to particular process steps and data structures described herein. Implementation of the process steps and data structures described herein would not require undue experimentation or further invention.

System Elements

Figure 1:
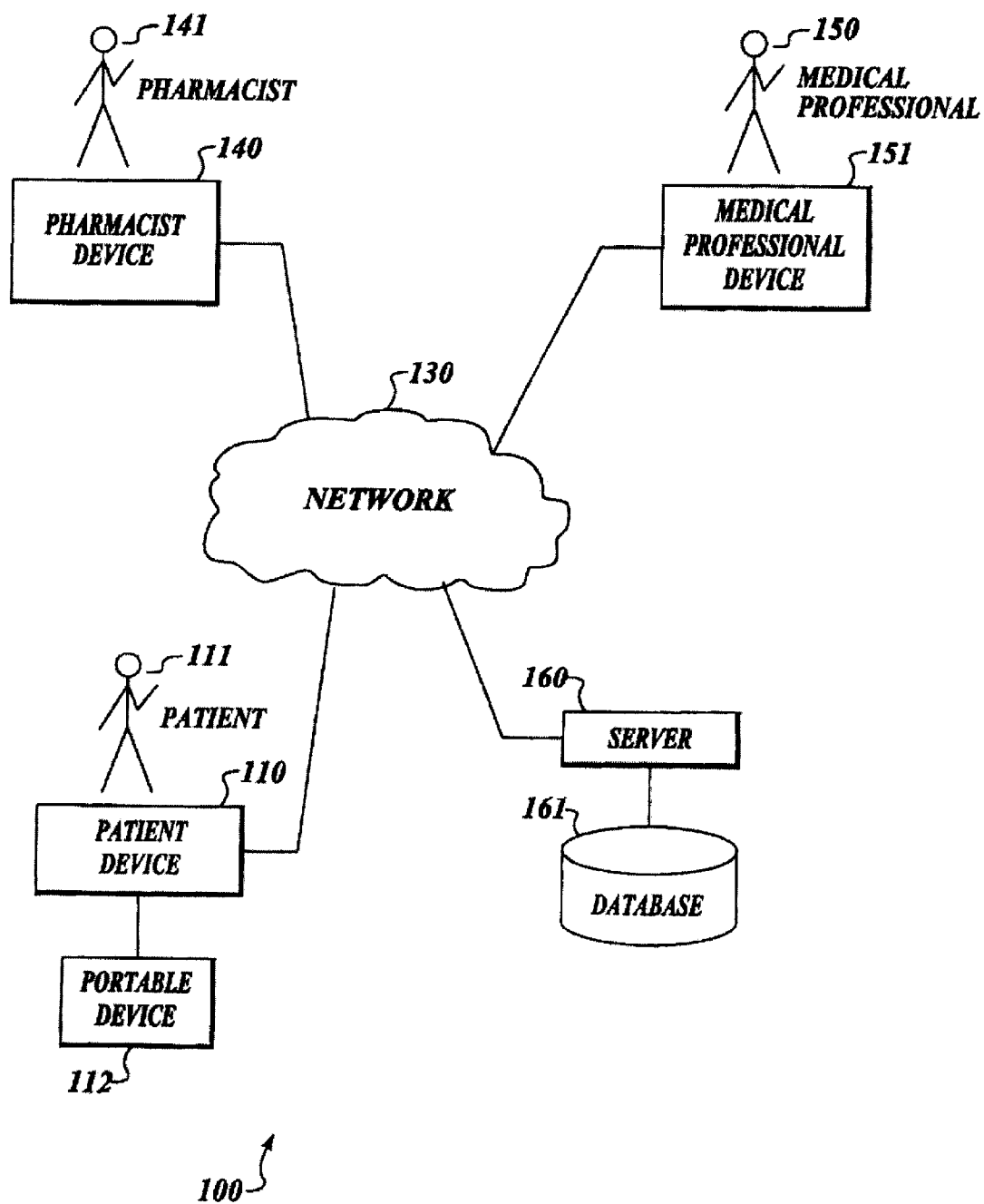
FIG. 1 shows a block diagram of a system for interaction with a community of individuals to encourage and monitor compliance with a treatment regimen, using a protocol or other intelligent message which acts in place of a service provider to collect and impart information relevant to the treatment regimen.

FIG. 1 shows a block diagram of a system 100 to encourage and monitor compliance with a treatment regimen using a protocol or other intelligent message which acts in place of a service provider to collect and impart information relevant to the treatment regimen, including a patient device 110, a pharmacist device 140, a medical professional device 150, and a server device 160, said devices being coupled using a communication network 130, and a portable device 112 which can be coupled to the patient device 110 to receive information regarding the treatment regimen and send feedback from the patient 111 responsive thereto.

For further information regarding a data structure and simplified patient interaction interface, and preferred embodiments of the patient device 110, pharmacist device 140, medical professional device 150, and the server device 160 including database 161 of treatment regimen information, see related application Ser. No. 09/201,323, Express Mail Mailing No. EE143637591US, filed Nov. 30, 1998, in the name of Stephen J. Brown, titled "Leveraging Interaction with A Community of Individuals," assigned to the same assignee, and other related applications incorporated by reference therein.

For further information regarding the protocol or other intelligent message used by the system, see related application Ser. No. 09/203,882, Express Mail Mailing No. EE143637565US, filed Dec. 1, 1998, in the name of Stephen J. Brown, titled "Remote User Data Collection Protocols Including Data Structures and User Interface," assigned to the same assignee, and other related applications incorporated by reference therein.

For further information regarding a medicine dispenser which can be used by the system, see related application Ser. No. 09/203,880, Express Mail Mailing No. EE143637557US, filed Dec. 1, 1998, in the name of Stephen J. Brown, et al., titled "Using A Computer Communication System With Feedback to Dispense Medicine," assigned to the same assignee, and other related applications incorporated by reference therein.

Portable Device

Figure 3:
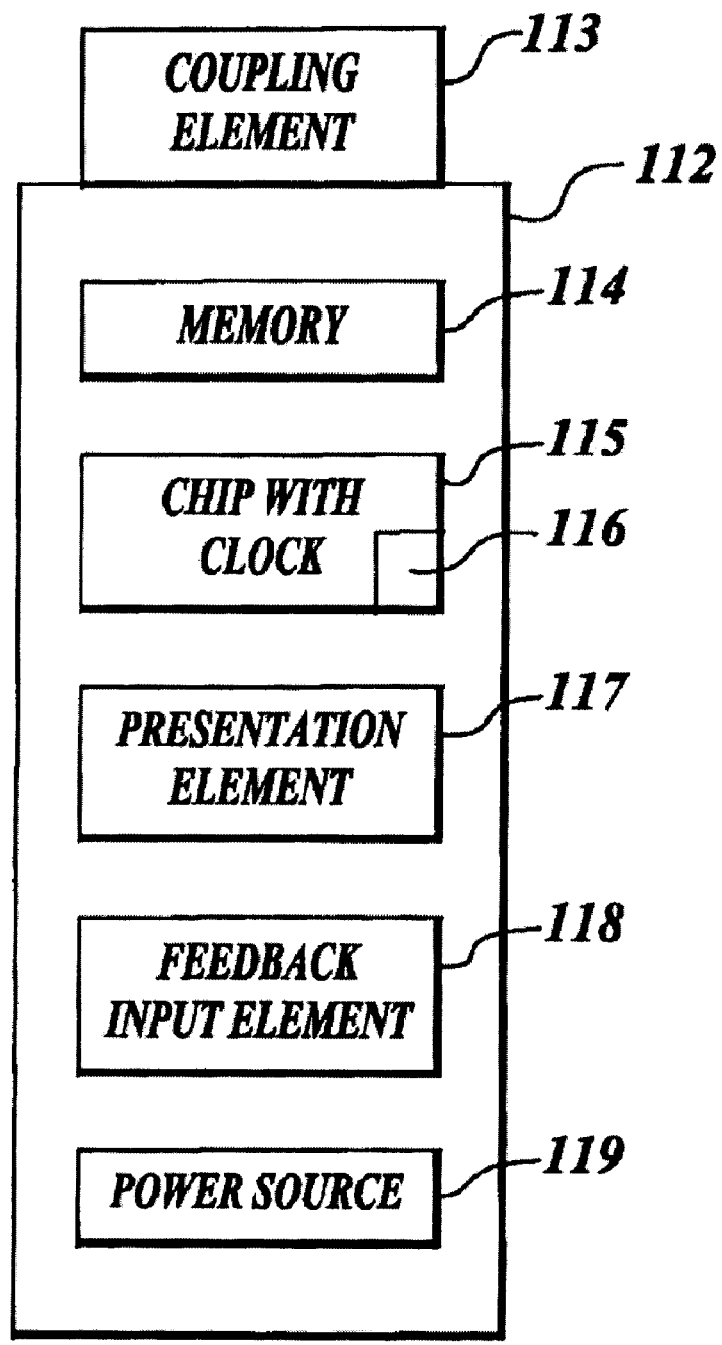
FIG. 3 shows a first preferred embodiment of a portable device used by the system to encourage and monitor compliance with a treatment regimen, and to collect and impart information relevant to the treatment regimen.

FIG. 3 shows a first preferred embodiment of a portable device 112 used by the system 100.

In a first preferred embodiment, the portable device 112 includes a coupling element 113 for coupling the portable device 112 to the patient device 110, a memory element 114, a processor chip 115 including a clock circuit 116, a presentation element 117, and a patient feedback input element 118.

A service provider determines a treatment regimen for selected patients 111 and a protocol to be followed by their portable devices 112 to assist the patients 111 in following the treatment regimen. The service provider sends the treatment regimen and protocol to the server device 160 where it is recorded in the database 161. The server device 160 sends the treatment regimen and protocol information to the patient device 110, and optionally to the pharmacist device 140 and the medical professional device 150.

The portable device 112 is coupled to the patient device 110 using the coupling element 113. The coupling element 113 may couple using a docking station, an infrared connection, a radio-frequency connection, a plug-in connection, other suitable means or any variant thereof.

While coupled, the treatment regimen and protocol information received by the patient device 110 is sent to the portable device 112 and recorded in the memory 114. In a first preferred embodiment, the power source 119 is rechargeable and the charge can be replenished by the patient device 110 while the portable device 112 is coupled to it. In alternative embodiments, the power source 119 is rechargeable and the charge can be replenished by some other device, or includes one or more disposable batteries.

After the treatment regimen and protocol information is recorded in the memory 114, the portable device 112 can be uncoupled from the patient device 110 and taken with the patient 110 to locations relatively or logically remote from the patient device 110. Whether the portable device 112 coupled or uncoupled to the patient device 110, when the patient 111 is due to perform an act according to the treatment regimen, the portable device 112 uses the presentation element 117 to provide a reminder message instructing the patient 111 to perform that act. In a first preferred embodiment, the act to be performed is related to compliance with a medication regimen including, without limitation, obtaining medicine, taking medicine, taking medicine with another substance such as food or water, not taking medicine with another substance such as alcohol or incompatible medications, or obtaining a prescription refill. In alternative embodiments, the act to be performed may be pursuant to a physical therapy regimen including, without limitation, exercising, stretching, changing position, or changing work routine; pursuant to a psychological therapy regimen including, without limitation, repeating an affirmation, meditation, self-hypnosis or other mental activity; or pursuant to a self-help regimen or other type of treatment regimen such as weight loss including, without limitation, drinking water or eating a snack.

The patient 111 performs the indicated act and enters a message into the portable device 112 confirming performance of the act using the patient feedback input element 118. Operation of the patient feedback input element 118 causes the processor chip 115 to cancel the reminder message, check the clock 116, and record the time and fact of performance in the memory 114. In a first preferred embodiment, the patient 111 also enters additional information relevant to monitoring and evaluating the treatment regimen in response to queries by the presentation element 117 in accordance with the treatment regimen and protocol.

The number of reminder messages provided to the patient 111, and the number of messages from the patient 111 confirming performance of the indicated acts and/or providing other information relevant to compliance with and effectiveness of the treatment regimen, is limited only by the memory capacity of the portable device 112.

In a first preferred embodiment, the presentation element 117 is a human-readable visual display using LCD's, LED's, or other suitable devices. In alternative preferred embodiments, the presentation element 117 can be a device which produces human-intelligible sound, or a combination of devices which produce human-intelligible visual and audible signals.

At some later time, the portable device 112 is re-coupled to the patient device 110 using the coupling element 113, causing the contents of the memory 114 to be downloaded into the patient device 110 and sent to the server device 160 for recording in the database 161. Such a time may be as is convenient to the patient 111, or according to a selected maximum time interval dictated by the treatment regimen and protocol, or as is required to replenish the power source 119 of the portable device 112, or in accordance with other requirements of the system 100.

At the server device 160, the protocol or other intelligent message reviews and compares the information provided by the patient 111 to the requirements of the treatment regimen in order to evaluate the effectiveness of the treatment regimen towards achieving treatment objectives and as to compliance of the patient 111 with the treatment regimen. The protocol may then leave the treatment regimen unchanged or modify it as needed to increase effectiveness and/or compliance; in either case, the server device 160 sends a message to the patient device 110 as to the regimen to be followed from that time forward. In a preferred embodiment, the server device 160 also sends that message to the pharmacist device 140 and the medical professional device 150. For additional information regarding the protocol used by the system 100 and interaction of the protocol with other elements of the system 100, see discussion above at System Elements regarding related applications.

In a first preferred embodiment, information regarding the entire course of the treatment regimen, such as each updated regimen and its effectiveness and relative compliance by the patient can be stored by each of those devices and displayed on demand. In alternative embodiments, only the server records the entire course, or only selected devices, or some combination thereof.

In a preferred embodiment, when a treatment regimen requires a patient 111 to take one or more medications, the portable device 112 can be coupled to a medication dispenser containing medication specified by the treatment regimen. In an alternative embodiment, the portable device 112 also controls the medication dispenser so as to release only the correct dosage of the correct medication at the correct time responsive to the treatment regimen. In a further alternative preferred embodiment, the dispenser automatically provides feedback to the portable device 112 when the correct medication is removed, canceling the reminder message and storing the feedback for subsequent downloading to the patient device 110 on the next occasion that the portable device 112 is coupled to the patient device 110.

The patient device 110 can be any device for electronic communication including, but not limited to, an application specific device, a hard-wired telephone, a cellular telephone, a pager, a personal desktop computer, a personal notebook computer, a hand-held computing device, an internet appliance, an internet-enabled television such as WebTV, personal digital assistant such as the Palm III, or any variant thereof.

The portable device 112 can be any portable device for electronic communication which is capable of being coupled to the patient device 110 including, without limitation, an application specific device, a cellular telephone, a pager, a personal notebook computer, a hand-held computing device, an interne appliance, a personal digital assistant such as the Palm III, a watch, or any variant thereof.

The feedback input element 118 can be any means of providing input to an electronic communication device including, but not limited to, a button, a telephone key, a computer keyboard key, a voice-response activator, or any variant or combination thereof.

Method of Operation

Figure 2:
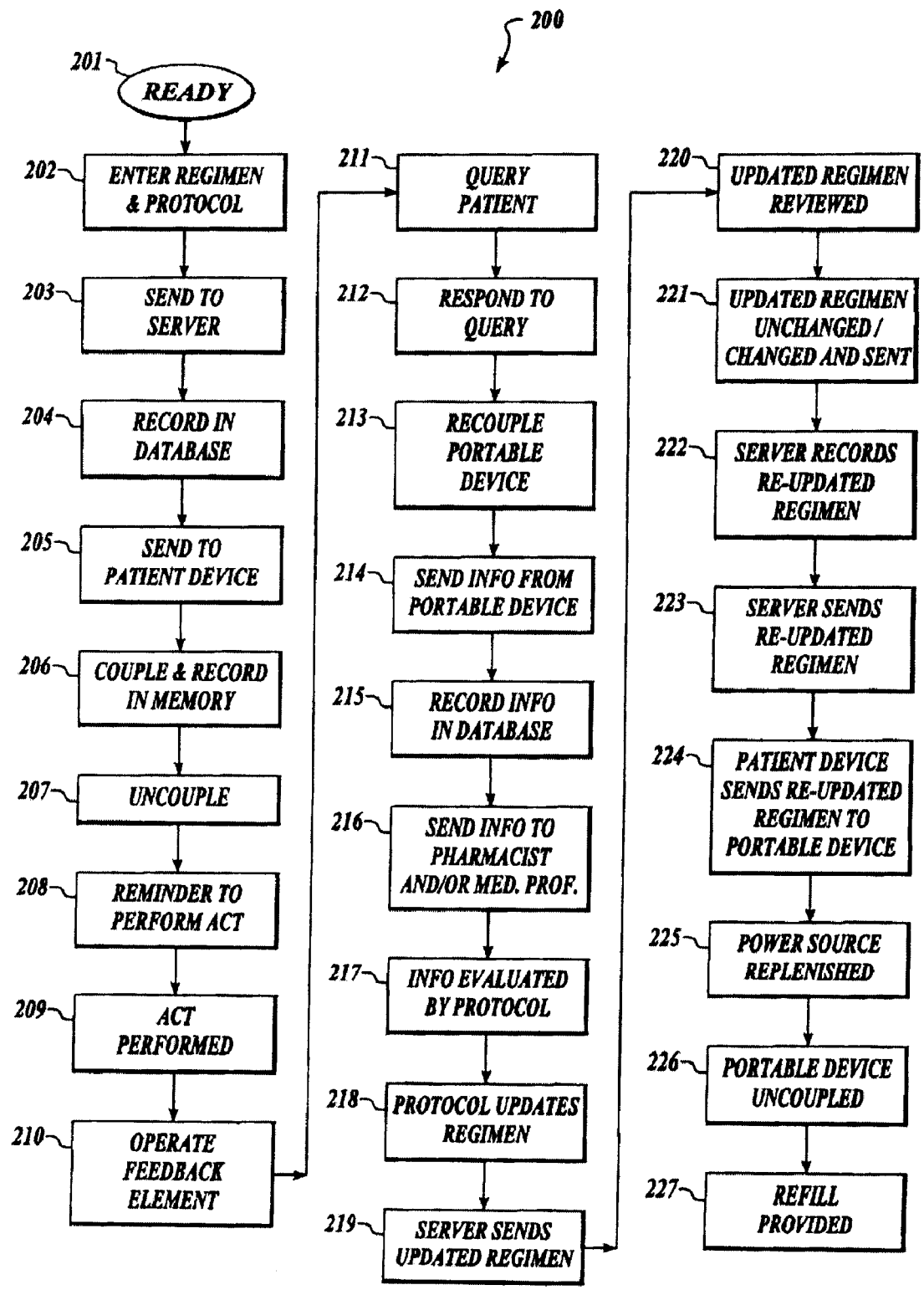
FIG. 2 shows a process flow diagram of a method for operating a system for interaction with a community of individuals to encourage and monitor compliance with a treatment regimen, using a protocol or other intelligent message which acts in place of a service provider to collect and impart information relevant to the treatment regimen.

FIG. 2 shows a process flow diagram of a method for operating a system for leveraging expert interaction with a community of individuals to encourage compliance with a treatment regimen and for collecting and imparting information relevant to that treatment regimen.

A method 200 is performed by the system 100, as follows:

At a flow point 201, the system 100 is ready to proceed.

At a step 202, a service provider enters information concerning a treatment regimen and protocol to be followed by the patient 111.

At a step 203, the treatment regimen and protocol information is sent to the server device 160 using the communications network 130.

At a step 204, the server device 160 records the treatment regimen and protocol information received from the service provider in the database 161.

At a step 205 in a preferred embodiment, the server device 160 sends the treatment regimen and protocol information to the patient device 110, the pharmacist device 140 and the medical professional device 150 using the communication network 130. In alternative embodiments, the server device 160 may send the treatment regimen and protocol information only to the patient device 110.

At a step 206, the portable device 112 is coupled to the patient device 110 and the treatment regimen and protocol information is copied into the memory 114 of the portable device 112.

At a step 207, the portable device 112 is uncoupled from the patient device 110 and is taken with the patient 111 to a location relatively remote from the patient device 110.

At a step 208, responsive to the treatment regimen and protocol information stored in the memory 114 in conjunction with input from the clock 116, the patient device 110 uses the presentation element 117 to provide a reminder message to the patient 111 that an act is required to be performed by the patient 111 and instructs the patient 111 regarding the act to be performed.

At a step 209, the patient 111 performs the indicated act as directed.

At a step 210, the patient 111 operates the feedback input element 118 on the portable device 112, canceling the reminder message.

At a step 211, the portable device 112 uses the presentation element 117 to query the patient 111 to provide information responsive to the protocol for evaluating the effectiveness of the treatment regimen.

At a step 212, the patient 111 operates the feedback input element 117 to provide information responsive to the queries, and that information is recorded in the memory 114.

At a step 213, the portable device 112 is re-coupled to the patient device 110.

At a step 214, the information stored in the memory 114 is sent to the patient device 110, which in turn sends that information to the server device 160 using the communication network 130.

At a step 215, the information received by the server device 160 is recorded in the database 161.

At a step 216, in a preferred embodiment the server device 160 sends the information received from the patient device 110 to the pharmacist device 140 and to the medical professional device 150 using the communication network 130. In an alternative embodiment, the server device 160 does not send the information received from the patient device 110 to the pharmacist device 140 or to the medical professional device 150, whether using the communication network 130 or otherwise.

At a step 217, the information received by the server device 160 from the patient device 110 is evaluated by the protocol.

At a step 218, the protocol updates the treatment regimen and either leaves it unchanged or modifies it in accordance with the protocol logic.

At a step 219 in a preferred embodiment, the server device 160 sends the updated treatment regimen information to the patient device 110, to the pharmacist device 140 and to the medical professional device 150, using the communication network 130. In an alternative embodiment, the server device 160 does not sent the updated treatment regimen information to the pharmacist device 140 or the medical professional device 150.

At a step 220 in a preferred embodiment, the pharmacist 141 and/or the medical professional 151 review and compare the original treatment regimen, the compliance and other information input by the patient 111, and the updated treatment regimen, and either leave the updated treatment regimen and protocol information unchanged or modify it as necessary. In an alternative embodiment, step 220 does not take place.

At a step 221 in a preferred embodiment, the treatment regimen and protocol information as unchanged or as modified by the pharmacist 141 and/or the medical professional 151 is sent to the server device 160 using the communication network 130. In an alternative embodiment, step 221 does not take place.

At a step 222, the server device 160 records the treatment regimen and protocol information as unchanged or as modified by the pharmacist 141 and/or the medical professional 151 in the database 161. In an alternative embodiment, step 222 does not take place.

At a step 223 in a preferred embodiment, the server device 160 sends the treatment regimen and protocol information as unchanged or as modified by the pharmacist 141 and/or the medical professional 151 to the patient device 110 using the communication network 130. In an alternative embodiment, step 223 does not take place.

At a step 224, the patient device 110 sends the updated treatment regimen information to the portable device 112 and it is recorded in the memory 114.

At a step 225, the patient device 110 replenishes the charge of the power source 119.

At a step 226, the patient 111 uncouples the portable device 112 from the patient device 110.

At a step 227, the pharmacist 141 provides a refill or new medicine to the patient 111 responsive to the treatment regimen and protocol information. In an alternative embodiment, step 227 does not take place.

Alternative Embodiments

Although preferred embodiments are disclosed herein, many variations are possible which remain within the concept, scope, and spirit of the invention, and these variations would become clear to those skilled in the art after perusal of this application.

The invention claimed is:

1. A system comprising:
 a server configured to determine if a patient is complying with a treatment regimen;
 a handheld device configured to (i) monitor and encourage compliance with said treatment regimen, (ii) inform said patient when to follow said treatment regimen, and (iii) generate a first data in response to a patient input, said handheld device comprising (i) a processor, (ii) a computer-readable memory, (iii) a presentation element, and (iv) an input element, wherein the computer-readable memory is programmed with a set of instructions and an identification code associated with the set of instructions, and the set of instructions, when executed by said processor, cause the processor to present at least one query and a plurality of predetermined responses corresponding to the at least one query to the patient via the presentation element and receive at least one of the predetermined responses corresponding to the at least one query as the patient input via the input element;
 a data management device configured to be coupled to said handheld device, wherein said data management device is configured to (i) receive said set of instructions and said identification code from said server, (ii) program said computer-readable memory of said handheld device with said set of instructions and said identification code, (iii) receive said first data and said identification code from said handheld device, and (iv) send said first data and said identification code to said server; and
 a network configured to connect said data management device to said server.

2. The system according to claim 1, wherein said server is further configured to determine if said treatment regimen has desired and intended effects.

3. A system comprising:
a data management device configured to receive a set of computer instructions concerning a treatment regimen and an identification code associated with the set of computer instructions from a server and a first data from a handheld device;
said handheld device configured to (i) receive said set of computer instructions concerning said treatment regimen and the identification code associated with the set of computer instructions from said data management device, (ii) inform a patient when to follow said treatment regimen, and (iii) generate said first data in response to a patient input, said handheld device comprising (i) a processor, (ii) a computer-readable memory, (iii) a presentation element, and (iv) an input element, wherein the computer-readable memory is programmed with said set of computer instructions and the identification code associated with the set of computer instructions, and the computer instructions, when executed, cause the processor to present at least one query and a plurality of predetermined responses corresponding to the at least one query to the patient via the presentation element and receive at least one of the predetermined responses corresponding to the at least one query as the patient input via the input element, wherein the first data sent to the data management device comprises the at least one of the predetermined responses corresponding to the at least one query received as the patient input via the input element and the identification code associated with the set of computer instructions; and
a coupling element configured to connect said data management device to said handheld device.

4. The system according to claim 3, wherein said coupling element comprises a docking station and said data management device comprises a personal desktop computer.

5. The system according to claim 3, wherein said coupling element comprises an infrared connection and said handheld device comprises a personal digital assistant.

6. The system according to claim 3, wherein said coupling element comprises a radio-frequency connection and said handheld device comprises a cellular telephone.

7. The system according to claim 3, wherein said coupling element comprises a plug-in connection and said data management device comprises a hard-wired phone.

8. The system according to claim 3, wherein said data management device connects to said server via a network.

9. A handheld device comprising:
a processor;
a memory in communication with the processor and configured to store a set of computer instructions corresponding to a treatment regimen and an identification code associated with the set of computer instructions;
a presentation element in communication with the processor and configured to display a set of queries and a plurality of sets of predetermined responses, each corresponding to one of the queries in the set of queries, wherein a patient can interact with said handheld device to select particular predetermined responses for each query in the set of queries;
an input element in communication with the processor and via which said patient can input information regarding said treatment regimen and select the particular predetermined responses to answer said set of queries; and
a coupling element configured to connect to a server, wherein said memory is programmed with instructions that cause the processor to present the set of queries and the plurality of sets of predetermined responses corresponding to the set of queries to the patient via the presentation element, receive the particular predetermined responses selected by the patient from the sets of predetermined responses corresponding to the set of queries, and transmit the particular predetermined responses selected by the patient and the identification code associated with the set of computer instructions to the server.

10. The handheld device according to claim 9, wherein said memory is a flash memory.

11. A method for encouraging patient compliance with a treatment regimen, comprising the steps of:
(A) providing first information about said treatment regimen to a data management device, wherein said first information comprises computer instructions and an identification code associated with the computer instructions;
(B) sending said first information to a handheld device from said data management device, wherein said computer instructions when executed by a processor of said handheld device cause the processor to present at least one query and a plurality of predetermined responses corresponding to the at least one query to the patient via a presentation element of the handheld device and receive at least one of the predetermined responses corresponding to the at least one query as an answer to the query via an input element of the handheld device;
(C) receiving second information from a patient at said handheld device regarding compliance with said treatment regimen;
(D) sending said second information from said handheld device and said identification code associated with the computer instructions to said data management device; and
(E) evaluating patient compliance with said treatment regimen based on said second information.

12. The method according to claim 11, further comprising the step of:
(F) controlling a medicine dispenser coupled to said handheld device in response to said second information.

13. The method according to claim 11, further comprising the step of:
(G) presenting a reminder at said handheld device regarding said treatment regimen.

14. A system comprising:
a server configured to send a first information about a treatment regimen, receive a second information and evaluate compliance with said treatment regimen based on said second information, wherein said first information comprises a set of computer instructions containing at least one query and a plurality of predetermined responses corresponding to the at least one query and an identification code associated with the set of computer instructions; and
a data management device configured to receive said first information, generate said second information regarding compliance with said treatment regimen, and send said second information and said identification code associated with the set of computer instructions to said server, wherein said set of computer instructions when executed cause said data management device to (i) query a patient with said at least one query and corresponding plurality of predetermined responses and (ii) receive a response selected by said patient as an answer to said at least one query.

15. The system according to claim 14, wherein said data management device is further configured to generate said second information in response to said response of said patient.

16. The system according to claim 14, wherein said server updates said first information based on said second information.

17. The system according to claim 14, wherein said data management device connects to said server by a coupling element.

18. The system according to claim 17, wherein said coupling element comprises a docking station and said data management device comprises a personal desktop computer.

19. The system according to claim 17, wherein said coupling element comprises an infrared connection and said data management device comprises a personal digital assistant.

20. The system according to claim 17, wherein said coupling element comprises a radio-frequency connection and said data management device comprises a cellular telephone.

* * * * *